United States Patent [19]

Kusunoki

[11] Patent Number: 5,401,274
[45] Date of Patent: Mar. 28, 1995

[54] HIGH-FREQUENCY TREATING INSTRUMENT

[75] Inventor: Hiroyuki Kusunoki, Tokyo, Japan

[73] Assignee: Olympus Optical Co., Ltd., Tokyo, Japan

[21] Appl. No.: 4,465

[22] Filed: Jan. 14, 1993

[30] Foreign Application Priority Data

Apr. 20, 1992 [JP] Japan .................................. 4-099412

[51] Int. Cl.⁶ ............................................ A61B 17/36
[52] U.S. Cl. ........................................ 606/41; 606/45; 606/46; 606/48
[58] Field of Search ................ 604/20, 21; 606/32–34, 606/41, 45–49, 50; 128/783–786, 804, 4, 6; 607/104, 105, 115, 116

[56] References Cited

U.S. PATENT DOCUMENTS

| | | | |
|---|---|---|---|
| 2,828,747 | 4/1958 | August | 606/45 |
| 3,532,095 | 10/1970 | Miller et al. | 606/45 |
| 4,054,143 | 10/1977 | Bauer | |
| 4,538,610 | 9/1985 | Kubota | 606/46 |
| 4,638,802 | 1/1987 | Okada | 606/47 |
| 5,135,524 | 8/1992 | Bonnet | 606/46 |
| 5,197,963 | 3/1993 | Parins | 606/46 |

FOREIGN PATENT DOCUMENTS

| | | |
|---|---|---|
| 0463363 | 2/1992 | European Pat. Off. |
| 7334752 | 12/1973 | Germany |
| 3217105A1 | 11/1983 | Germany |
| 8202488 | 8/1982 | WIPO |

*Primary Examiner*—Stephen C. Pellegrino
*Assistant Examiner*—Michael Peffley
*Attorney, Agent, or Firm*—Frishauf, Holtz, Goodman & Woodward

[57] ABSTRACT

A high-frequency treating instrument comprises an insertion tube having electric conductivity, an electrically insulating, tubular member fitted over an outer periphery of the insertion tube with a distal open end of the tubular member projected ahead of a distal end of the insertion tube, a current supply section for supplying a high-frequency current which is fed from a power source to the insertion tube, an electrode section fixedly provided on the distal end of the insertion tube to carry the high-frequency current there, the electrode section being projected out of the distal open end of the tubular member to allow the high-frequency current which is fed from the power source to be received through the insertion tube, and a treating section provided on the distal end of the electrode section projected out of the distal open end of the tubular member and allowing the high-frequency current to be carried therethrough so that an affected living tissue of a human subject can be treated through heat resulting from the high-frequency current.

8 Claims, 4 Drawing Sheets

HIGH-FREQUENCY TREATING INSTRUMENT

BACKGROUND OF THE INVENTION

1. Field of the Invention

The present invention relates to a high-frequency treating instrument for, for example, resecting/separating or blood-coagulation treating an affected living body tissue by a high-frequency current.

2. Description of the Related Art

The tip of the high-frequency treating instrument is usually inserted into a human body cavity via an aperture hole in the wall of a body cavity and, for example, resects, separates and cauterizes or blood-coagulation treats an affected body cavity tissue through the use of a high-frequency current.

As shown, for example, in U.S. Pat. Nos. 4811733, 5071419, International Publication WO82/02488 and European patent application Ser. No. 0463363A2 the high-frequency treating instrument has an electrode section provided on a distal end side of an insertion section inserted into a body cavity and composed of an electroconductive member, in which, through the passage of a high-frequency current through the electrode section, the electrode section heats an affected body cavity tissue through contact and resects, separates or blood-coagulation treats it.

One form of the high-frequency treating instrument is shown in FIG. 14 of European Patent Application No. 0463363A2.

The high-frequency treating instrument has an insertion tube inserted into the body cavity and an electrode section provided within the distal end portion of the insertion tube to allow conduction. In order to secure an electrical conduction between the electrode section and the insertion tube, the insertion tube is made of an electroconductive material and a high-frequency current is supplied to the electrode section through the insertion tube.

A J shaped treating section is provided on the distal end of the electrode section so as to treat an affected region of the human body. The forward end side of the electrode section is projected out of the distal open end of the insertion tube. Of the electrode section projecting out of the distal open end of the insertion section, that outer peripheral portion other than the treating section is covered with an insulating material. An insulating material is covered on the outer peripheral portion and inner wall portion of the insertion tube inserted into the body cavity so as to secure electrical safety.

In the case where the affected living tissue of the human body is resected or separated by the high-frequency treating instrument, a high-frequency current is supplied via the insertion tube to the electrode section and the electrode section is heated. The treating section at the distal end of the electrode section not covered with the insulating material is set in contact with a region of a human body tissue. By so doing, the body tissue region is resected and separated under an action of heat by the electrode section. When, however, the end face of the insertion tube allowing the electrode section to be electrically connected is brought in contact with the living tissue, there is a risk that the contacting site will be cut or resected.

Heretofore, an insulating coating has been used as the insulating material with which the electrode section and insertion tube are covered. However, the insulating coating is hard to deposit, for example, on the end face and inner surface of the distal end section of the insertion tube, thus presenting an electrically insulating hazard problem. Further, it takes a lot of time to perform the coating operation itself. In addition to this, defects also are involved in the coated area.

SUMMARY OF THE INVENTION

It is accordingly the object of the present invention to provide a high-frequency treating instrument excellent in electrical insulation.

The object of the present invention is achieved by the high-frequency treating instrument as will be set out below. That is, the present instrument comprises an insertion tube having electrical conductivity, an electrically insulating, tubular member fitted over an outer periphery of the insertion tube with a distal open end of the tubular member projected ahead of a distal end of the insertion tube, a current supply means for supplying a high-frequency current which is fed from a power source to the insertion tube, an electrode section fixedly provided on the distal end of the insertion tube to carry the high-frequency current there, the electrode section being projected out of the distal open end of the tubular member to allow the high-frequency current which is fed from the power source to be received through the insertion tube; and a treating section provided on the distal end of the electrode section projected out of the distal open end of the tubular member and allowing the high-frequency current to be carried therethrough so that an affected living tissue of a human subject can be treated through heat resulting from that high-frequency current.

In the high-frequency treating instrument of the present invention, the electrically insulating, tubular member is fitted over the outer periphery of the insertion tube such that the distal end of the tubular member is projected ahead of the insertion tube so that any area of the insertion tube is completely insulated relative to an outside and hence any area of the insertion tube carrying a high-frequency current therethrough is not brought into contact with a living body tissue. It is, thus, possible to prevent an electric current from being flowed into a living body tissue through direct contact by the insertion tube.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE PREFERRED EMBODIMENTS

The embodiments of the present invention will be explained below with reference to the accompanying drawings.

Figures 1, 2:
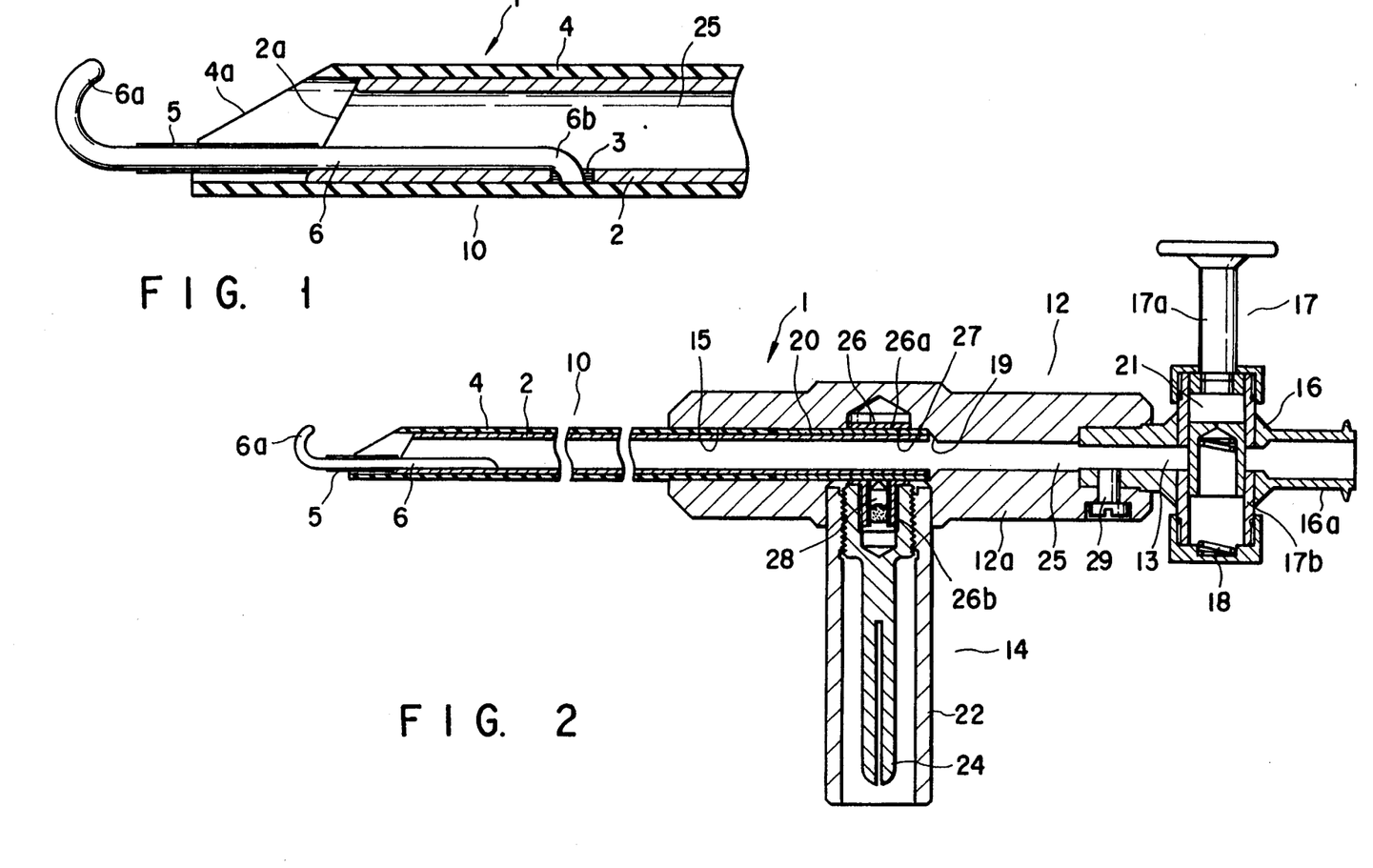
FIG. 1 is a cross-sectional view showing a major area of a high-frequency treating instrument according to a first embodiment of the present invention.
FIG. 2 is a cross-sectional view showing a whole arrangement of the high-frequency treating instrument according to the first embodiment of the present invention.

FIGS. 1 to 4 show a first embodiment of the present invention. As shown in FIG. 2, a high-frequency treating instrument 1 of the present invention has an insertion section 10 inserted into a body cavity of a human being. An operation section 12 is provided on the proximal end side of the insertion section 10. A power source cord mount section 14 and a tubular member 16 equipped with a valve member 17 are connected to an operation section body 12a of the operation section 12. The insertion section 10 of the high-frequency treating instrument 1 is comprised of an insertion tube 2 of an electroconductive material and an insulating tube 4 made of an insulating material is fitted over the outer periphery of the insertion tube 2. The distal end of the insertion tube 2 is located more toward the proximal side than that of the insulating tube 4, that is, retracted back into the insulation tube 4.

An electrode section 6 is provided in the distal end of the insertion tube 2 and is made of a conductive material. As shown in an enlarged view in FIG. 1, the base end portion 6b of the electrode section 6 is fixedly bonded to a connection hole 3 in the inner wall of the insertion tube 2 to allow conduction. By so doing, a high-frequency current is supplied from an outside source through the insertion tube 2 to the electrode section 6. The distal end portion of the electrode section 6 extends axially along the inner surface of the insertion tube 2 and is projected out of the distal open end 2a of the insertion tube 2 and further ahead out of a distal open end 4a of the insulating tube 4. The insertion tube 2 and insulating tube 4 have their diagonally cut distal faces.

The distal end portion of the electrode section 6 projected out of the distal open end 4a of the insulating tube 4 is bent back in an inward direction to provide a treating section 6a of the electrode section 6 as a bent-back area. Of the electrode portion projected out of the distal open end 2a of the insertion tube 2, that outer peripheral portion of the electrode section 6 is covered with the insulating member 5 except the treating section 6a. The insulating member 5 may be formed by covering an insulating coating on the outer peripheral portion of the electrode section 6, but it is preferable that the insulating member 5 be comprised of an insulating tube-like member fitted over the outer periphery of the electrode section 6.

As shown in FIG. 2, a through bore 15 is provided in the operation body section 12a in a longitudinal direction with a stepped area 19 formed at a substantially middle in the inner surface of the through bore. The through bore 15 has an inner diameter somewhat larger at the distal end side than at the proximal end side with the stepped area 19 as a reference in which case the inner diameter at the distal end side is substantially equal to the outer diameter of the insulating tube 4. The proximal end portion of the insulating tube 4 is inserted into the distal end portion of the through bore 15 in which case the outer diameter of the proximal end portion of the insulating tube 4 is substantially the same as the inner diameter of the through bore 15. The proximal end portion of the insertion tube 2 extends via the base end of the insulating tube 4 to the proximal end side of the through bore 15 past an insertion hole 27 (see FIG. 4) of a pipe receiving section 26a of a contact member 26, as will be set out below, which is provided partway of the through bore 15, the end face of the proximal end of the insertion tube 2 abutting against the end face of the stepped section 19 of the through bore 15.

Between the inner surface of the through bore 15 and though hole 27 and the outer peripheral portion of the proximal end side of the insertion tube 2 a ring-like sleeve 20 is provided so as not to leave a gap therebetween, the ring-like sleeve 20 being made of an electroconductive material. In this state, the insertion tube 2 is mechanically and fixedly connected to the operation section body 12a by a mounting means as will be set out below.

The inner diameter of a portion of the through bore 15 at the proximal end side relative to the stepped area 19 is substantially the same as the inner diameter of the insertion tube 2 and a fluid passage 25 for a high-frequency treating instrument 1 is provided by both a portion of the through bore 15 at the proximal end side relative to the stepped area 19 and the inner bore of the insertion tube 2.

The tubular member 16 is connected by a fastening means 29 to the base end of the operation section body 12a. A channel 13 of the tubular member 16 communicates with the through bore 15 of the operation section body 12a. The channel 13 of the tubular member 16 has an inner diameter substantially equal to the inner diameter of the through bore 15.

The valve member 17 is provided at an area of the tubular member 16 and comprises a piston section 17a and a cylinder section 17b. Normally, the valve member 17 is placed in a closed state in which it shuts off communication between the channel 13 on the base end side relative to the valve member 17 and the channel 13 on the distal end side relative to the valve member 17. The piston section 17a, upon being compressed against an urging force of a spring means 18 into the cylinder section 17b to align a communication hole 21 of the piston section 17a with the channel 13, enables the channel 13 at the base end side relative to the valve member 17 to communicate with the channel 13 at the distal end side relative to the valve member 17. If a hose is connected to a connector 16a at the proximal end of the tubular member 16, for example, to a suction device to align the communication hole 21 of the piston section 17a with the channel 13, then the hose communicates with the fluid passage 25 so that waste matter, etc., in the body cavity of the human being can be sucked through the fluid passage 25.

The power source mount section 14 is connected to the operation section body 12a in a vertical relation to the through bore 15. The power source cord mount section 14 constitutes a means for supplying a high frequency current to the insertion tube 2 and also constitutes the aforementioned mount means for fixedly connecting the insertion tube 2 to the operation section body 12a.

Figure 3:
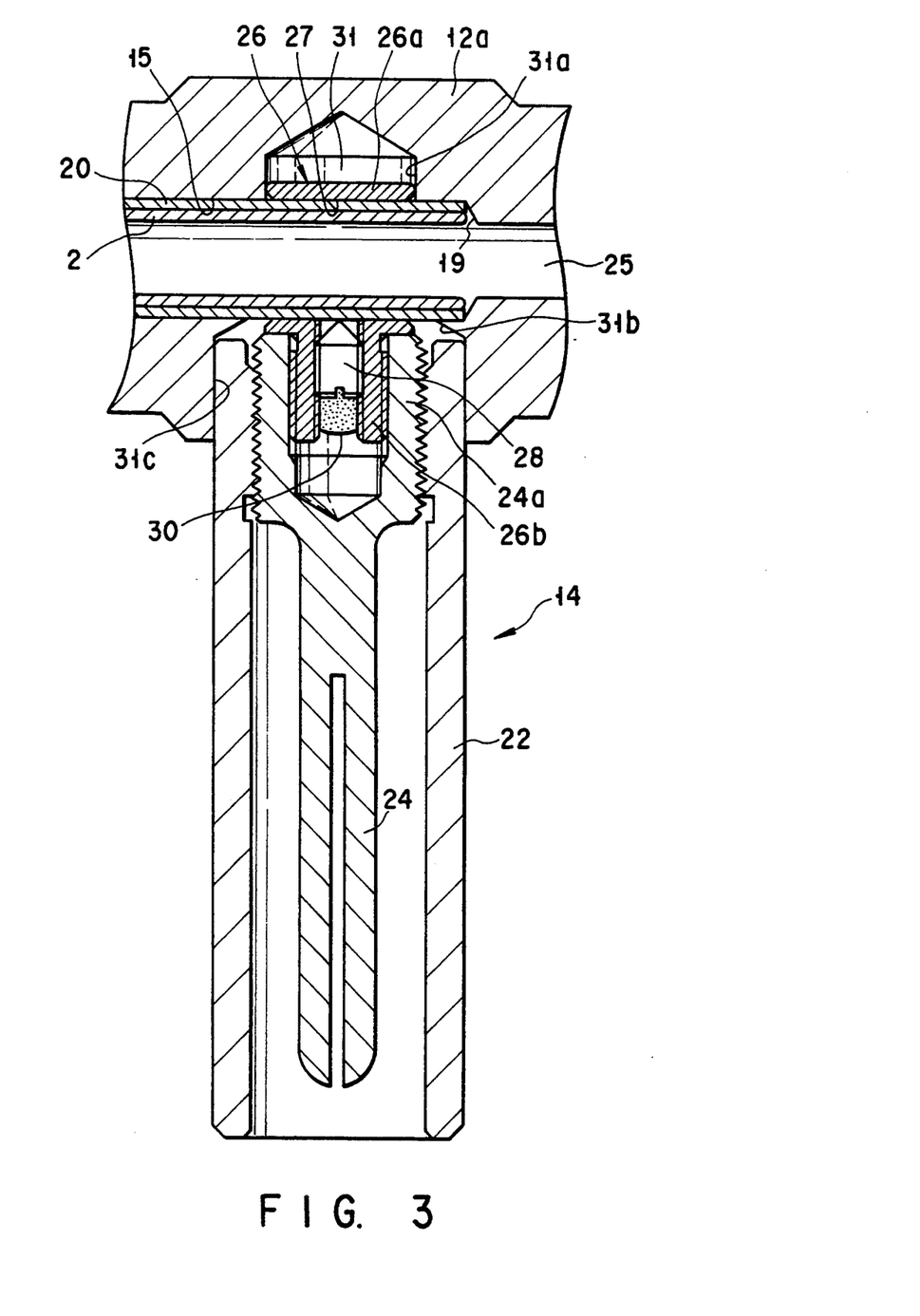
FIG. 3 is an enlarged, cross-sectional view showing a power source cord mount section in the treating instrument of FIG. 1.
Figure 4:
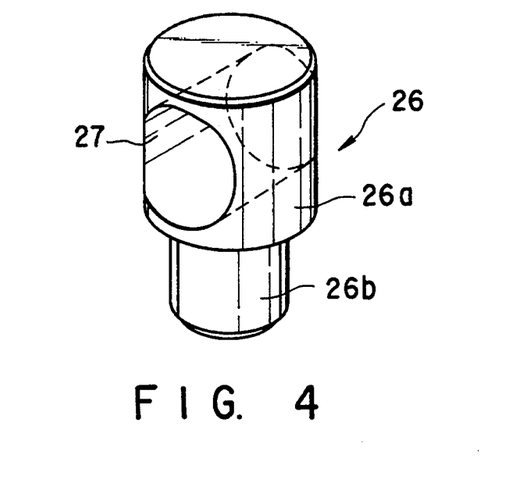
FIG. 4 is a perspective view showing a contact member in the treating instrument of FIG. 1.

As shown in an enlarged from in FIG. 3, the power source cord mount section 14 has a conductive contact member 26 made of a conductive metal, a cord mount pin 24 and an electrically insulating cover 22. The contact member 26 comprises a large-diameter pipe receiving section 26a and a small-diameter connection section 26b as shown in FIG. 4. The pipe receiving section 26a has a through hole 27 in a direction perpendicular to the axis of the contact member 26. The through hole 27 has an inner diameter substantially the same as that of the through bore 15 at the distal end side relative to the stepped area 19.

The contact member 26, cord mount pin 24 and cover 22 are mounted in a mount hole 31 of the operation section body 12a. The mount hole 31 is formed vertically from the outer surface of the operation section body 12a toward the through bore 15 and has its inner end located on the opposite end side relative to the through bore 15 such that the mount hole 31 communicates with the through bore 15 at the distal end side relative to the stepped area 19, that is, the through hole 31 is formed vertically across the through bore 15 at the distal end side relative to the stepped area 19. The mount hole 31 is comprised of a small-diameter inner section 31a located at the opposite side of the through bore 15 and a large-diameter outer section 31c located at that externally open end side of the operation section body 12a. The inner face of the large-diameter outer section 31c at the through bore 15 side is narrowed in its diameter to provide a taper face 31b.

The small-diameter inner section 31a has an inner diameter substantially the same as the outer diameter of the pipe receiving section 26a of the contact member 26. The head section of the pipe receiving section 26a is inserted into the small-diameter inner section 31a. In this state, the through hole 27 in the pipe receiving section 26a is aligned with the through bore 15 of the operation section body 12a. The base end portions of the insertion tube 2 and sleeve 20 inserted into the through hole 15 extend through the insertion hole 27 in which case the contact member 26 is held in a state to be supported on the base end portion of the sleeve 20 inserted through the through bore 15. In order to fix the contact member 26 to the sleeve 20, a fastening screw means 28 is threaded into the inner hole of the small-diameter connection section 26b communicating with the insertion hole 27. That is, the contact member 26 is fixed to the sleeve 20 by threading the screw means 28 toward the outer surface of the sleeve 20 and abutting the tip of the screw means 28 against the outer surface of the sleeve 20. In order to prevent the loosening of the screw means 28, a bonding agent 30 is filled in the inner hole of the small-diameter connection section 26b.

The connection section 26b of the contact member 26 thus supported is located within the large-diameter outer section 31c of the mount hole 31. A mount section 24a of the cord mount pin 24 is threaded over the outer peripheral portion of the connection section 26b. The end portion of the cover 22 is threaded over the outer peripheral portion of the mount section 24a of the cord mount pin 24. The cover 22 has an outer diameter substantially equal to the inner diameter of the large-diameter outer section 31c of the mount hole 31. When the cover 22 is inserted into the outer section 31c while being threadably inserted over the outer peripheral portion of the mount section 24a of the cord mount pin 24, to cause the end face of the cover 22 to be pushed against a taper section 31b then the cord mount pin 24 and contact member 26 in threaded engagement with the pin 24 are pushed toward the sleeve 20 side so that the inner surface of the insertion hole 27 of the contact member 26 serving as an electrical contact is pressed against the outer surface of the sleeve 20. A pushing force acting, at this time, upon the outer surface of the sleeve 20 enables the outer peripheral surface of the sleeve 20 at its one-side area (at its upper-side area in FIG. 3) to push against the inner surface of the through bore 15 and hence the insertion tube 2 is pressed against the inner surface of the through bore 15 through the sleeve 20. By so doing, the insertion tube 2 is fixed to the operation section body 12a.

The operation of the high-frequency treating instrument 1 will be explained below.

When an affected tissue of a human body cavity, for example, is to be resected with the use of a high-frequency treating instrument, the insertion section 10 is inserted into the body cavity via an aperture pierced through the wall of the human body such that the distal end of the insertion section 10 is located close to a region of the affected tissue of the human body. Then the affected tissue is located within the bent-back hook of the treating section 6a of the electrode section 6. Before such a series of operations, a power source cord connected to the power source device is electrically and mechanically connected to the cord mount pin 24 of the power source cord mount section 14 which is connected to the operation section 12 of the high-frequency treating instrument 1.

After the affected tissue of the human being is located within the bent-back hook of the treating section 6a of the electrode section 6, a high-frequency current is supplied, by the power source cord, from the power source device to the high-frequency treating instrument 1. In this case, the high-frequency current is supplied from the power source device through the power source cord, cord mount pin 24, contact member 26 and sleeve 20. The high-frequency current which is supplied to the insertion tube 2 is carried to the electrode section 6 so that the electrode section 6 is heated. If, with the electrode section 6 heated, the insertion section 10 is pulled toward the proximal end side so that the treating section 6a is brought into contact with the affected tissue region, then the affected tissue region can be resected by the treating section 6a.

Since, in the aforementioned arrangement, the insulating tube 4 is fitted over the outer peripheral portion of the insertion tube 2 which is inserted into the body cavity and through which the high-frequency current is carried, the outer surface area of the insertion tube 2 is not set in direct contact with the tissue region of the human body cavity. Further, the outer surface of the insertion tube 2 is electrically insulated not by applying the insulation coating to the outer periphery of the insertion tube 2 but by fitting the insulating tube 4 (tubular member) over the outer surface of the insertion tube 2. Thus there is no possibility that the insulating coating will be peeled off the outer periphery of the insertion tube 2 or be damaged due to its imperfect deposition. Since the distal end portion of the insertion tube 2 is inserted into the insulating tube 4, there is no risk that the distal end face, etc., of the insertion tube 2 will be brought into contact with the region of the body tissue. That is, the distal end face of the insertion tube 2 and inner surface of the distal end portion of the insertion tube 2 which have been hard to cover with the insulating coating are also insulated completely.

According to the present invention, instead of covering the insulating coating on the outer periphery of the insertion tube 2 as in the prior art so as to electrically insulate the insertion tube 2, the insulating tube 4 (tubular member) is fitted over the outer periphery of the insertion tube 2 with the distal end 4a of the insulating tube 4 located ahead of the distal end 2a of the insertion tube 2 so that the insertion tube 2 is electrically insulated. This enables complete insulation to be achieved on the outer peripheral portion of the insertion tube 2 as well as on the distal end face of the insertion tube 2 and inner surface of the distal end portion of the insertion tube 2 which have been hard to cover with the insulating coating. Since any area of the insertion tube 2 through which a high-frequency current is carried is not set in contact with the region of the body tissue, no electric current flows to the region of the body tissue through direct contact of the insertion tube 2 with the region of the body tissue.

In the present invention, as the electrode section 6 other than the treating section 6a is also insulated by the insulating member 5 and hence all the conductive area except the treating section 6a is completely insulated, electrical insulation can be achieved on the whole treating instrument 1. Therefore, any normal body tissue other than the affected region is not injured, thus ensuring a safer operation.

Further, the insulation of the insertion tube 2 is achieved simply by fitting the insulating tube 4 over the outer periphery of the insertion tube 2. It is, therefore, not necessary to perform any cumbersome operation of applying an insulating coating which often involves a defective result. That is, according to the present invention, it is possible to positively achieve the insulation of the insertion tube 2 by a readier operation.

The mechanical connection of the insertion tube 2 to the operation section body 12a and that of the insertion tube 2 to the power source cord mount section 14 are achieved without the use of any bonding agent, thereby enhancing electrical conductivity, improving an assembling operation and ensuring added reliability.

Figure 5:
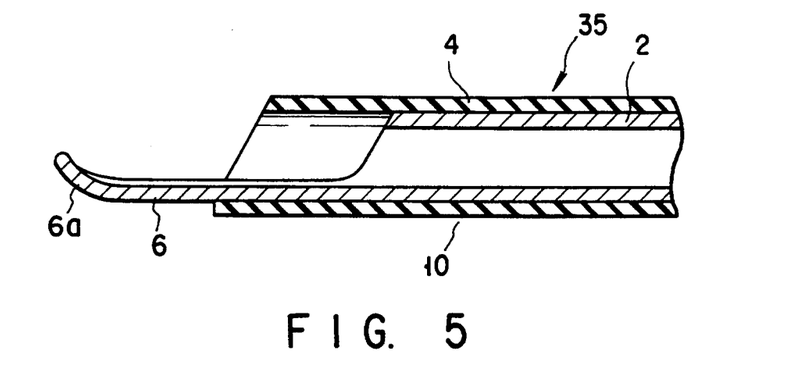
FIG. 5 is a cross-sectional view showing a major area of a high-frequency treating instrument according to a second embodiment of the present invention.

FIG. 5 shows a second embodiment of the present invention. In the high-frequency treating instrument 35, an insertion tube 2 is formed integral with an electrode section 6. The second embodiment of the present invention is similar to the first embodiment thereof except the insertion tube 2 integral with the electrode section 6 as set out above. An insulating material may be, for example, covered on the outer periphery of the electrode section 6 other than a treating section 6a.

Figure 6:
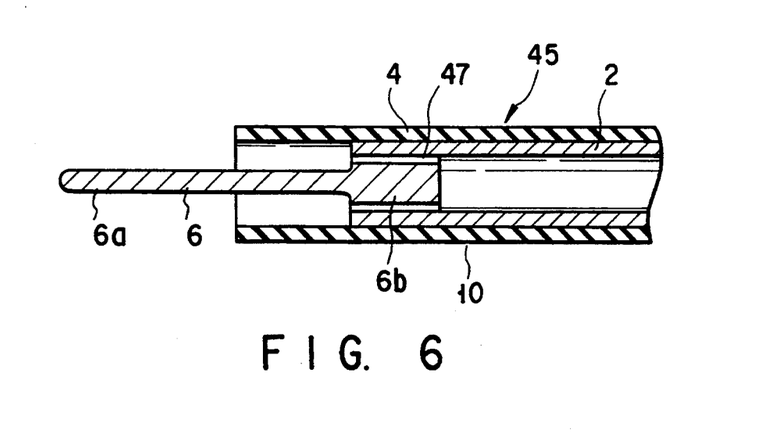
FIG. 6 is a cross-sectional view showing a major area of a high-frequency treating instrument according to a third embodiment of the present invention.

FIG. 6 shows a third embodiment of the present invention. A high-frequency treating instrument 45 of the third embodiment is similar to that of the first embodiment except that a base end portion 6b of an electrode section 6 is fixedly fitted into the distal end portion of an insertion tube 2. In this case, communication grooves 47 are provided in the outer periphery surface of a base portion 6b of the electrode section 6 to allow communication to be made between a fluid passage 25 and an outside. An insulating material may be, for example, covered on the outer peripheral surface of the electrode section 6 other than a treating section 6a.

Needless to say, the aforementioned high-frequency treating instruments 35 and 45 of the second and third embodiments have the same advantages as those of the first embodiment.

Figure 7:
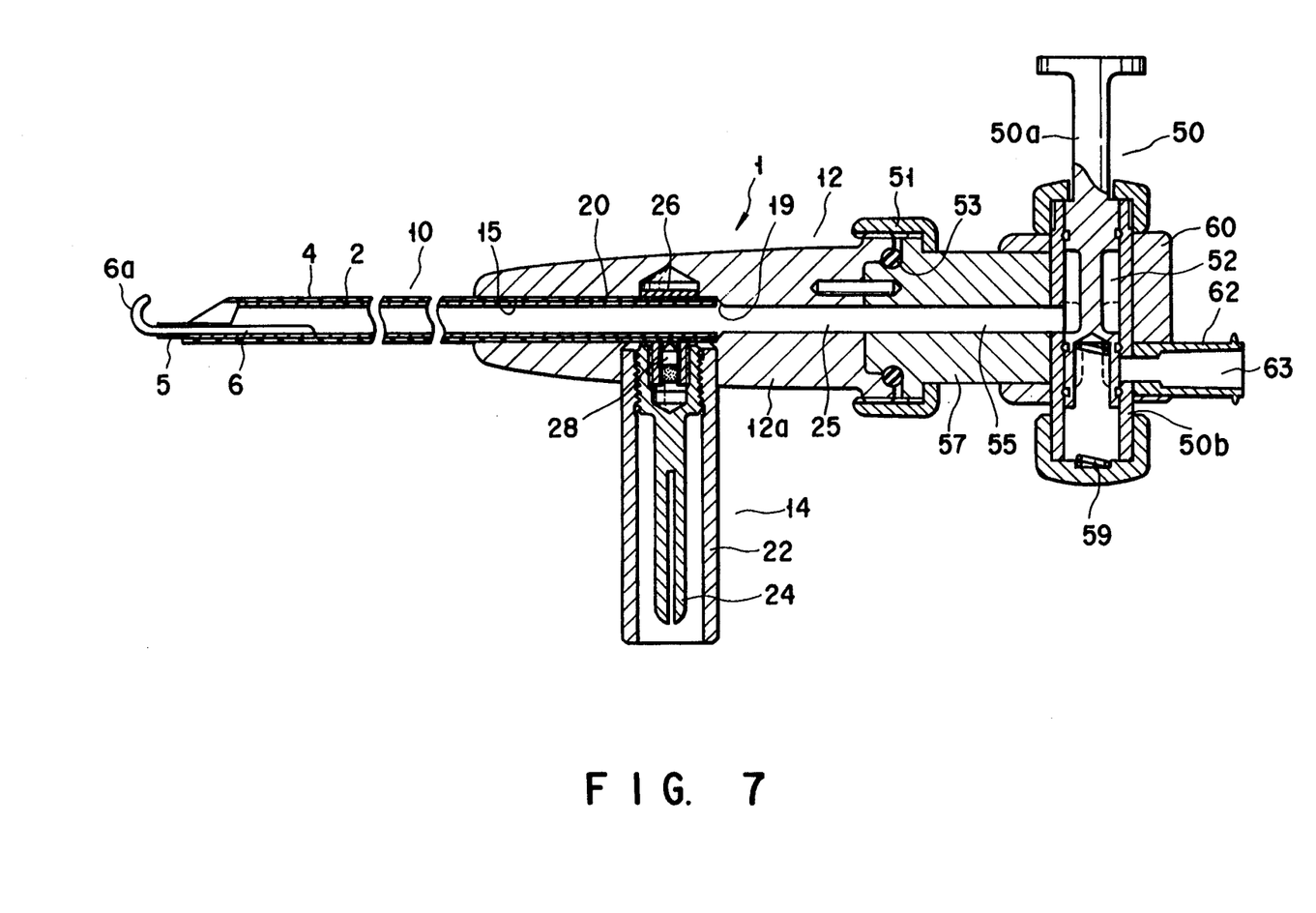
FIG. 7 is a cross-sectional view showing a variant of an operation section of the high-frequency treating instrument of FIG. 2.

FIG. 7 shows a variant of a tubular member 16 connected to an operation section body 12a. As shown in FIG. 7, a cylinder body 57 is connected by a connection member 51 to the operation section body 12a. A communication hole 55 is provided in the cylinder body 57 and has an inner diameter substantially the same as that of a fluid passage 25. In a connection state shown, the communication hole 55 communicates with the fluid passage 25 and an O-ring 53 is interposed at an area between the cylinder body 57 and the operation section body 12a.

A valve body 60 equipped with a valve member 50 is connected to the end of the cylinder body 57 and a cylindrical connector 62 is provided at the valve body 60. The valve member 50 comprises a piston 50a and cylinder section 50b and an annular communication groove 52 is provided in the outer peripheral surface of the piston section 50a. With the piston section 50a not pushed inwardly, that is, the piston section 50a set in a standby state shown, communication is created between the communication groove 52 of the piston section 50a and the communication hole 55 of the cylinder body 57, while, on the other hand, communication is shut off between an inner hole 63 of the connector 62 and the communication hole 55 of the cylinder body 57. When the piston section 50a is pushed, against the urging force of a spring means 59, into the cylinder section 50b to such an extent that the communication groove 52 communicates with the inner hole 63 of the connector 62, then the inner hole 63 of the connector 62 communicates with the communication hole 55 of the cylinder body 57 through the annular communication groove 52 in the piston section 50a. The suction operation using the valve member 50 is similar to that using the valve member 17 in FIG. 2.

As already set out in connection with the respective embodiment of the present invention, the insulating tubular member 4 is fitted over the outer periphery of the insertion tube 2 in the high-frequency treating instrument so that the outer face of the insertion tube 2 is not placed in direct contact with the living tissue. Thus there is no possibility that electrical insulation will be broken due to the peeling and defective deposition, etc., of a film such as an insulating coating. This is not because electrically insulation on the outer surface of the insertion tube 2 is achieved by covering the insulating coating on the outer periphery of the insertion tube 2 but because such electrical insulation is achieved by fitting the insulating tubular member 4 over the outer periphery of the insulation tube 2. Further, the distal end of the insertion tube 2 is located within the insulating tubular member 4 and hence, for example, the distal end face of the insertion tube 2 is not brought in contact with the living tissue. Complete insulation is achieved on the distal end face of the insertion tube 2 and inner surface portion of its distal end portion which have been hard to cover with the insulating coating. As a result, no electric current flows across the living tissue through the insertion tube 2 because any region of the insertion tube 2 carrying a high-frequency current is not brought in contact with that living tissue.

According to the present invention, insulation is achieved on the insertion tube 2 simply by fitting the insulating tube 4 over the outer periphery of the insertion tube 2. It is not necessary to perform any cumbersome operation of covering the insulating coating which has experienced a defective result. That is, according to the present invention, positive insulation can be achieved on the insertion tube by an easy operation.

The present invention is not restricted to the aforementioned embodiments and various changes or modifications can be made without departing from the spirit and scope of the present invention.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A high-frequency treating instrument comprising:
an electrically conductive insertion tube;
an electrically insulating, tubular member fitted over an outer periphery of the insertion tube with a distal open end of the tubular member projected ahead of a distal end of the insertion tube;
a power source for supplying a high-frequency current which is fed from the power source to the insertion tube;
an electrode section fixedly provided on the distal end of the insertion tube for receiving the high-frequency current from the insertion tube, the electrode section being projected out of the distal open end of the tubular member to allow the high-frequency current which is fed from the power source to be received through the insertion tube; and
a treating section provided on a distal end of the electrode section that is projected out of the distal open end of the tubular member and allowing the high-frequency current to be carried therethrough so that an affected living tissue of a human subject can be treated with heat generated as the high-frequency current flows therethrough; and wherein
the power source comprises a connection section for making an electrical connection to the insertion tube; and
the power source connection section comprises:
a contact member for making an electrical connection to the insertion tube;
a mount pin threadably inserted over an outer periphery of the contact member; and
a mount cover threadably inserted over an outer periphery of the mount pin.

2. A high-frequency treating instrument comprising:
an electrically conductive insertion tube;
an electrically insulating, tubular member fitted over an outer periphery of the insertion tube with a distal open end of the tubular member projected ahead of a distal end of the insertion tube;
said electrically insulating tubular member having a taper-cut distal end face;
a power source coupled to the insertion tube for supplying a high-frequency current to the insertion tube;
an electrode section fixedly provided on the distal end of the insertion tube for receiving the high-frequency current from the insertion tube, the electrode section being projected out of the distal open end of the tubular member to allow the high-frequency current which is fed from the power source to be received through the insertion tube;
a treating section provided on a distal end of the electrode section that is projected out of the distal open end of the tubular member and allowing the high-frequency current to be carried therethrough so that an affected living tissue of a human subject can be treated with heat generated as the high-frequency current flows therethrough; and
a grip section having a through bore through which the insertion tube is inserted and a mount hole provided across the through bore; and wherein:
the electrode section is fitted into the mount hole; and
the electrode section further comprises:
a contact member for making an electrical connection to the insertion tube;
a mount pin threadably inserted over an outer periphery of the contact member; and
a mount cover threadably inserted over an outer periphery of the mount pin and fitted into an inner surface of the mount hole.

3. The high-frequency treating instrument according to claim 2, wherein the electrode section further comprises:
a connector for fixedly connecting the insertion tube to the grip section by fitting the mount cover into the mount hole, while being threadably inserted over the outer periphery of the mount pin; and
the mount pin and contact member being threaded into the mount pin and then being pushed by a pushing force toward the mount hole and hence the insertion tube, into contact with an inner surface of the through bore of the grip section.

4. The high-frequency treating instrument according to claim 2, wherein the contact member comprises a through hole formed therein and through which the insertion tube extends.

5. A high-frequency treating instrument comprising:
an electrically conductive insertion tube having an opening formed in a distal end thereof;
an electrically insulating, tubular member fitted over an outer periphery of the insertion tube with a distal open end of the tubular member projected ahead of the distal end of the insertion tube;
the electrically insulating tubular member having a taper-cut end face;
a flow passage formed in the insertion tube for permitting a fluid to flow into and out of said insertion tube through the opening in the distal end of said insertion tube;
a power source coupled to the insertion tube and supplying a high-frequency current to the insertion tube;
an electrode section fixedly provided on the distal end of the insertion tube for receiving the high-frequency current from said power source via the insertion tube, the electrode section being projected out of the distal open end of the tubular member to allow the high-frequency current which is fed from the power source to be received by the electrode section through the insertion tube;
a treating section provided on a distal end of the electrode section that is projected out of the distal open end of the tubular member and allowing the high-frequency current to be carried therethrough so that an affected living tissue of a human subject can be treated with heat generated as the high-frequency current flows therethrough; and wherein the electrode section comprises:
a contact member for making an electrical connection to the insertion tube;
a mount pin threadably inserted over an outer periphery of the contact member; and
a mount cover threadably inserted over an outer periphery of the mount pin.

6. A high-frequency treating instrument comprising:
an electrically conductive insertion tube having an opening formed in a distal end thereof;
an electrically insulating, tubular member fitted over an outer periphery of the insertion tube with a distal open end of the tubular member projected ahead of the distal end of the insertion tube;
the electrically insulating tubular member having a taper-cut end face;
a flow passage formed in the insertion tube for permitting a fluid to flow into and out of said insertion tube through the opening in the distal end of said insertion tube;
a power source coupled to the insertion tube and supplying a high-frequency current to the insertion tube;
an electrode section fixedly provided on the distal end of the insertion tube for receiving the high-frequency current from said power source via the insertion tube, the electrode section being projected out of the distal open end of the tubular member to allow the high-frequency current which is fed from the power source to be received by the electrode section through the insertion tube;
a treating section provided on a distal end of the electrode section that is projected out of the distal open end of the tubular member and allowing the high-frequency current to be carried therethrough so that an affected living tissue of a human subject can be treated with heat generated as the high-frequency current flows therethrough;
further comprising a grip section having a through bore through which the insertion tube is inserted and a mount hole provided across the through bore, the electrode section being fitted into the mount hole;
wherein the electrode section comprises:
a contact member for making an electrical connection to the insertion tube;
a mount pin threadably inserted over an outer periphery of the contact member; and
a mount cover threadably inserted over an outer periphery of the mount pin and fitted into an inner surface of the mount hole.

7. The high-frequency treating instrument according to claim 6, wherein the electrode section further comprises:
a connector for fixedly connecting the insertion tube to the grip section by fitting the mount cover into the mount hole, while being threadably inserted over the outer periphery of the mount pin; and
the mount pin and contact member being threaded into the mount pin and then being pushed by a pushing force toward the mount hole and hence the insertion tube, into contact with an inner surface of the through bore of the grip section.

8. The high-frequency treating instrument according to claim 7, wherein the contact member comprises a through hole formed therein and through which the insertion tube extends.

* * * * *